(12) United States Patent
Vaynberg et al.

(10) Patent No.: US 11,197,713 B2
(45) Date of Patent: *Dec. 14, 2021

(54) DEVICE AND METHOD FOR FRACTIONAL RF TREATMENT OF THE SKIN

(71) Applicant: VENUS CONCEPT LTD., Karmiel (IL)

(72) Inventors: Boris Vaynberg, Zichron Yakov (IL); Yotam Zimmerman, Hadera (IL)

(73) Assignee: Venus Concept Ltd., Yokeneam Illit (IL)

( * ) Notice: Subject to any disclaimer, the term of this patent is extended or adjusted under 35 U.S.C. 154(b) by 77 days.

This patent is subject to a terminal disclaimer.

(21) Appl. No.: 14/251,937

(22) Filed: Apr. 14, 2014

(65) Prior Publication Data

US 2014/0309628 A1    Oct. 16, 2014

Related U.S. Application Data

(60) Provisional application No. 61/811,750, filed on Apr. 14, 2013.

(51) Int. Cl.
| | | |
|---|---|---|
| *A61B 18/14* | (2006.01) | |
| *A61N 1/32* | (2006.01) | |
| *A61B 18/00* | (2006.01) | |
| *A61B 18/12* | (2006.01) | |
| *A61N 1/05* | (2006.01) | |

(52) U.S. Cl.
CPC .................. *A61B 18/1477* (2013.01); *A61B 2018/00011* (2013.01); *A61B 2018/00029* (2013.01); *A61B 2018/00916* (2013.01); *A61B 2018/124* (2013.01); *A61B 2018/143* (2013.01); *A61B 2018/1467* (2013.01); *A61N 1/0502* (2013.01); *A61N 1/328* (2013.01)

(58) Field of Classification Search
CPC .. A61B 2018/1427; A61B 2018/00011; A61B 2018/00916; A61B 2018/00922; A61B 18/124; A61B 18/143
See application file for complete search history.

(56) References Cited

U.S. PATENT DOCUMENTS 4,561,445 A * 12/1985 Berke .................. A61B 5/0492
163/5
6,142,992 A * 11/2000 Cheng ................ A61B 18/1206
606/34

(Continued)

*Primary Examiner* — Michael F Peffley
*Assistant Examiner* — Bo Ouyang
(74) *Attorney, Agent, or Firm* — Foley & Lardner LLP

(57) ABSTRACT

A system and method for treating the skin by heating at least one discrete skin volume, comprising at least one treatment tip reversibly connectable to at least one applicator. The treatment tip comprises one or more electrodes, with the electrodes having one or more spaced apart protruding conducting elements. The protruding conducting elements are characterized by dimensions of height A and hypotenuse B, where the ratio A/B is in a predetermined range, and the protruding conducting elements penetrate the skin surface at discrete locations. The electrodes are configured to apply energy to skin volumes around the discrete locations so as to heat the skin volumes. The applicator comprises an energy generator configured to apply energy to the skin volumes by means of the electrodes and the spaced apart protruding conducting elements.

27 Claims, 10 Drawing Sheets

(56) References Cited

U.S. PATENT DOCUMENTS

| | | | | |
|---|---|---|---|---|
| 6,167,291 | A * | 12/2000 | Barajas | A61B 5/04286 |
| | | | | 439/909 |
| 6,572,613 | B1 * | 6/2003 | Ellman | A61B 18/1477 |
| | | | | 606/41 |
| 2004/0162551 | A1 * | 8/2004 | Brown | A61B 18/1477 |
| | | | | 606/41 |
| 2007/0173811 | A1 * | 7/2007 | Couture | A61B 18/1445 |
| | | | | 606/39 |
| 2008/0091182 | A1 * | 4/2008 | Mehta | A61B 18/14 |
| | | | | 606/29 |
| 2008/0249523 | A1 * | 10/2008 | McPherson | A61B 18/1445 |
| | | | | 606/41 |
| 2008/0287943 | A1 * | 11/2008 | Weber | A61B 18/0218 |
| | | | | 606/41 |
| 2010/0049178 | A1 * | 2/2010 | Deem | A61B 18/02 |
| | | | | 606/9 |
| 2011/0015625 | A1 * | 1/2011 | Adanny | A61N 1/0476 |
| | | | | 606/33 |
| 2011/0202053 | A1 * | 8/2011 | Moss | A61B 18/1477 |
| | | | | 606/41 |
| 2011/0306968 | A1 * | 12/2011 | Beckman | A61B 18/1482 |
| | | | | 606/41 |
| 2012/0095459 | A1 * | 4/2012 | Callas | A61B 18/14 |
| | | | | 606/41 |

* cited by examiner

DEVICE AND METHOD FOR FRACTIONAL RF TREATMENT OF THE SKIN

FIELD OF THE INVENTION

The present invention relates generally to apparatus and methods for treating skin by application of energy to a fraction of the skin to cause heating, coagulation or resurfacing of the skin. The energy can be RF energy.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

A few main approaches to tightening of the skin are common practice today. The surgical approach carries disadvantages related to the anesthesia, the surgical complications, and the healing process, which may cause scars. The chemical peel approach usually involves injury to the outermost layer of the skin—the epidermis—which may cause discoloration.

A multitude of fractional ablative procedures are performed on the visible surfaces of various tissues in order to improve their appearance, e.g., as in cosmetic tissue resurfacing treatments. There are different energy-based devices used for skin treatment. One large group is laser-based devices, which include ablative lasers such as $CO_2$ lasers and non-ablative lasers such as fiber lasers. Such devices are efficient, producing good clinical results, but are limited to operation by qualified physicians only and usually have a high cost.

Recently, Radio Frequency electrical current devices were developed to provide results similar to those of laser-based devices. The electrical current is delivered to the tissue though an array of electrodes (sometimes needles). In contrast to lasers, in RF devices the electrical energy can be delivered to multiple locations in the tissue simultaneously, when all electrodes in the device are activated simultaneously. The disadvantage of such an approach is that, due to all the energy being delivered to the tissue simultaneously, treatment can be very painful. Also, since all the electrodes are connected electrically in parallel, the electrical current may differ in different electrodes due to variations in the impedance of the tissue below the electrodes, even if a current-controlled source is used. Finally, the device is usually adapted to operate over a limited range of impedances and therefore is not flexible enough to be used with different types or sizes of treatment tip.

It is therefore a long felt need to provide an improved apparatus and method for treating skin by application of energy to the skin to cause heating, coagulation or resurfacing of the skin. The energy can be RF energy.

SUMMARY OF THE INVENTION

It is an object of the present invention to disclose an apparatus and methods for treating skin by application of energy to the skin to cause heating, coagulation or resurfacing of the skin. The energy can be RF energy.

It is another object of the present invention to disclose a system for treating the skin by heating at least one discrete skin volume, comprising:

a. at least one treatment tip comprising N electrodes, N being an integer greater than or equal to 1; at least one said electrode having at least one spaced apart protruding conducting element; at least one said protruding conducting element is characterized by dimensions of height A and hypotenuse B, at least one said protruding conducting element is configured to penetrate the skin surface at at least one discrete location; at least one said electrode is configured to apply energy to said at least one discrete skin volume so as to heat said at least one discrete skin volume; and b. an applicator comprising at least one energy generator configured to apply said energy to said at least one skin volume by means of said at least one electrode and said at least one spaced apart protruding conducting element;

wherein the ratio A/B is in a predetermined range.

It is another object of the present invention to disclose the system, wherein said ratio A/B is in a range of about 0.9 to about 0.995.

It is another object of the present invention to disclose the system, wherein said treatment is RF treatment.

It is another object of the present invention to disclose the system, wherein at least one said energy generator supplies voltage in at least one of the following ranges:

a. the applied voltage is in a range from about 160 V and 320 V RMS;

b. the applied voltage is in a range from about 180 V and 300 V RMS; and c. the applied voltage is in a range from about 220 V and 280 V RMS.

It is another object of the present invention to disclose the system, wherein at least one of said protruding conducting elements is configured to cut through the stratum corneum of said skin.

It is another object of the present invention to disclose the system, wherein said at least one discrete skin volume is tissue located beneath said skin; further wherein said at least one discrete skin volume is tissue located beneath the stratum corneum of said skin.

It is another object of the present invention to disclose the system, wherein said applicator additionally comprises at least one control unit adapted to regulate the application of said energy.

It is another object of the present invention to disclose the system, wherein said control unit is adapted to monitor physical skin parameters and change applied energy accordingly.

It is another object of the present invention to disclose the system, additionally comprising at least one switch adapted to reversibly connect at least one said energy generator to at least one said electrode.

It is another object of the present invention to disclose the system, wherein at least one said switch is adapted to simultaneously connect a number M of electrodes to at least one said energy generator, where M is an integer in the range from 1 to N.

It is another object of the present invention to disclose the system, wherein the ratio M/N is in a range selected from a group consisting of: 1/N to about 10%; about 10% to about 25%, and greater than about 25%.

It is another object of the present invention to disclose the system, wherein at least one of the following is true:
a. N is about 40;
b. each said electrode comprises between about 1 and about 5 said protruding conducting elements;
c. each said electrode comprises 4 said protruding conducting elements;
d. the distance between said protruding conducting elements is about 1 mm; and,
e. the density of said protruding conducting elements is about 120 per cm$^2$.

It is another object of the present invention to disclose the system, wherein said protruding conducting element is shaped substantially as a prism characterized by a rectangular base of length L and width W, two four-sided side faces of length L, and two three-sided end faces of said height A, said hypotenuse B and width W, said base conjoined with said electrode.

It is another object of the present invention to disclose the system, wherein at least one of the following is true:
a. said length L is in a range of about 25 μm to about 500 μm;
b. said length L is about 150 μm;
c. said angle θ is in a range of about 10° to about 50°;
d. said angle θ is about 30'; and
e. said side faces of said triangular prism have a shape selected from a group consisting of flat, inwardly curving, outwardly curving and any combination thereof.

It is another object of the present invention to disclose the system, wherein said applicator additionally comprises at least one switching module comprising at least one switch, each said at least one electrode reversibly electrically connectable to at least one said energy generator by means of at least one said switch.

It is another object of the present invention to disclose the system, additionally comprising a mechanism for cooling at least a portion of said skin, said cooling mechanism selected from a group consisting of: a pre-cooled liquid applied directly to said skin; a pre-cooled liquid applied to said skin via tubes within said applicator, said tubes contacting said skin; a pre-cooled spray applied to said skin; a cryogenic spray applied to said skin; a thermo-electric contact cooler and any combination thereof.

It is another object of the present invention to disclose the system, wherein at least one of the following is true:
a. said electrode is made of material selected from a group consisting of stainless steel, copper, gold, conductive polymers and any combination thereof; and
b. said electrode comprises stainless steel.

It is another object of the present invention to disclose the system, wherein said treatment tip is reversibly electrically connectable to said switching module.

It is another object of the present invention to disclose the system, wherein said applicator additionally comprises at least one contactor adapted to provide said reversible electrical connection between at least one of said electrodes in said treatment tip and at least one of said switches in said switching module.

It is another object of the present invention to disclose the system, wherein at least one of the following is true:
a. said contactor has substantially the shape of a cylinder characterized by a main longitudinal axis;
b. said contactor is made of material selected from a group consisting of copper, steel, gold, conductive polymer and any combination thereof; and
c. said contactor comprises stainless steel.

It is another object of the present invention to disclose the system, wherein said contactor is in physical contact with said electrode on at least a portion of a side parallel to said main longitudinal axis.

It is another object of the present invention to disclose the system, additionally comprising at least one flexible connector, electrical connection between at said least one said switch and at least one said electrode is via said connector.

It is another object of the present invention to disclose the system, wherein said connector is characterized by spring-like properties.

It is another object of the present invention to disclose the system, additionally comprising a printed circuit board (PCB) adapted to provide electrical connection between said at least one switching module, said at least one energy generator and at least one said connector.

It is another object of the present invention to disclose the system, wherein at least one of the following is true:
a. a duration in a range of about 5 ms to about 30 ms between activating and deactivating at least one of said electrodes;
b. a delay time between deactivating and activating at least one of said electrodes in a range of about 1 ms to about 30 ms; and
c. a delay time of about 2 ms between deactivating and activating at least one of said electrodes.

It is another object of the present invention to disclose the system, wherein the distance between at least one first electrode being activated and at least one second electrode being activated is maximized.

It is another object of the present invention to disclose the system, wherein said device comprises more than one treatment tip to treat more than one body part simultaneously.

It is another object of the present invention to disclose the system, wherein at least one of the following is true:
a. said treatment tip is disposable;
b. said applicator is reusable;
and any combination thereof.

It is another object of the present invention to disclose a device for treating the skin comprising:
a. at least one treatment tip comprising N electrodes, N being an integer greater than or equal to 1, at least one said electrode having at least one spaced apart protruding conducting element; at least one said protruding conducting element is characterized by dimensions of height A and hypotenuse B, at least one said protruding conducting element is configured to penetrate the skin surface at least one discrete location; at least one said electrode is configured to apply energy to at least one discrete skin volume so as to heat said at least one discrete skin volume;
b. an applicator comprising an energy generator configured to apply said energy to said at least one skin volume by means of said at least one electrode and said at least one spaced apart protruding conducting element;
c. at least one switching module comprising at least one switch, each of said at least one electrodes is reversibly electrically connectable to said at least one energy generator by means of at least one of said switches; said applicator further comprising said switching module;
d. at least one contactor electrically connectable to at least one said electrode; and
e. at least one connector characterized by a proximal end and a distal end, said connector electrically connected at its proximal end to at least one said switch and electrically connected at its distal end to at least one said contactor;
wherein said connector is made of flexible material and said contactor and said electrode are made of stiff material, further wherein at least a portion of said energy is applicable to said at least one skin volume by means of said electrical connection.

It is another object of the present invention to disclose the device, wherein said connector is characterized by spring-like properties.

It is another object of the present invention to disclose the device, additionally comprising a printed circuit board (PCB) adapted to provide electrical connection between said at least one switching module, said at least one energy generator and at least one said connector.

It is another object of the present invention to disclose the device, wherein said treatment tip is reversibly electrically connectable to said switching module.

It is another object of the present invention to disclose the device, wherein at least one of the following is true:
a. said contactor has substantially the shape of a cylinder characterized by a main longitudinal axis;
b. said contactor is made of material selected from a group consisting of copper, steel, gold, conductive polymer and any combination thereof; and
b. said contactor comprises stainless steel.

It is another object of the present invention to disclose the device, wherein said contactor is in physical contact with said electrode on at least a portion of a side parallel to said main longitudinal axis.

It is another object of the present invention to disclose the device, wherein at least one of the following is true:
a. said electrode is made of material selected from a group consisting of stainless steel, copper, gold, conductive polymers and any combination thereof; and
b. said electrode comprises stainless steel.

It is another object of the present invention to disclose the device, wherein the ratio A/B is in a range of about 0.9 to about 0.995.

It is another object of the present invention to disclose the device, wherein said treatment is RF treatment.

It is another object of the present invention to disclose the device, wherein at least one said energy generator supplies voltage in at least one of the following ranges:
a. the applied voltage is in a range from about 160 V and 320 V RMS:
b. the applied voltage is in a range from about 180 V and 300 V RMS; and
c. the applied voltage is in a range from about 220 V and 280 V RMS.

It is another object of the present invention to disclose the device, wherein at least one of said protruding conducting elements is configured to cut through the stratum corneum of said skin.

It is another object of the present invention to disclose the device, wherein said at least one discrete skin volume is tissue located beneath said skin; further wherein said at least one discrete skin volume is tissue located beneath the stratum corneum of said skin.

It is another object of the present invention to disclose the device, wherein said applicator additionally comprises at least one control unit adapted to regulate the application of said energy.

It is another object of the present invention to disclose the device, wherein said control unit is adapted to monitor physical tissue parameters and change applied energy accordingly.

It is another object of the present invention to disclose the device, wherein at least one said switch is adapted to simultaneously connect a number M of electrodes to said energy generator, where M is an integer in the range from 1 to N.

It is another object of the present invention to disclose the device, wherein the ratio M/N is in a range selected from a group consisting of: 1/N to about 10%; about 10% to about 25%, and greater than about 25%.

It is another object of the present invention to disclose the device, wherein at least one of the following is true:
a. N is about 40;
b. each said electrode comprises between about 1 and about 5 said protruding conducting elements;
c. each said electrode comprises 4 said protruding conducting elements;
d. the distance between said protruding conducting elements is about 1 mm; and
e. the density of said protruding conducting elements is about 120 per cm$^2$.

It is another object of the present invention to disclose the device, wherein said protruding conducting element is shaped substantially as a prism characterized by a rectangular base of length L and width W, two four-sided side faces of length L, and two three-sided end faces of said height A, said hypotenuse B and width W, said base conjoined with said electrode.

It is another object of the present invention to disclose the device, wherein at least one of the following is true:
a. said length L is in a range of about 25 μm to about 500 μm;
b. said length L is about 150 μm;
c. said angle θ is in a range of about 10° to about 50°;
d. said angle θ is about 30°; and
e. said side faces of said prism have a shape selected from a group consisting of flat, inwardly curving, outwardly curving and any combination thereof.

It is another object of the present invention to disclose the device, additionally comprising a mechanism for cooling at least a portion of said skin, said cooling mechanism selected from a group consisting of: a pre-cooled liquid applied directly to said skin; a pre-cooled liquid applied to said skin via tubes within said applicator, said tubes contacting said skin; a pre-cooled spray applied to said skin; a cryogenic spray applied to said skin; a thermo-electric contact cooler and any combination thereof.

It is another object of the present invention to disclose the device, wherein at least one of the following is true:
a. a duration in a range of about 5 ms to about 30 ms between activating and deactivating at least one of said electrodes;
b. a delay time in the range of about 1 ms to about 30 ms between activating and deactivating at least one of said electrodes; and
c. a delay time of about 2 ms between activating and deactivating at least one of said electrodes.

It is another object of the present invention to disclose the device, wherein at least one of the following is true:
a. said treatment tip is disposable;
b. said applicator is reusable;
and any combination thereof.

It is another object of the present invention to disclose a method for reducing pain during skin treatment, comprising steps of:
a. providing a device for treating the skin, comprising:
    i. at least one treatment tip comprising N electrodes, N being an integer greater than or equal to 1, at least one said electrode having at least one spaced apart protruding conducting element; at least one said protruding conducting element is characterized by dimensions of height A and hypotenuse B, at least one said protruding conducting element is configured to penetrate the skin surface at at least one discrete location; at least one said electrode is configured to apply energy to at least one discrete skin volume so as to heat said at least one discrete skin volume;

ii. an applicator comprising at least one energy generator configured to apply energy to said at least one skin volume by means of said at least one electrode and said at least one spaced apart protruding conducting element;

iii. at least one switching module comprising at least one switch, each of said at least one electrodes is reversibly electrically connectable to said at least one energy generator by means of at least one of said switches; said applicator further comprising said switching module;

iv. at least one contactor electrically connectable to at least one said electrode; and v. at least one connector characterized by a proximal end and a distal end, said connector electrically connected at its proximal end to at least one said switch and electrically connected at its distal end to at least one said contactor;

b. connecting said treatment tip to said applicator;

c. activating at least one said energy generator such that electrical current is suppliable to at least one of said electrodes; and d. activating said switching module according to a predetermined sequence:

i. activating at least one of said switches, said activation creating an electrical connection between at least one said energy generator and at least one first electrode, thereby delivering energy to at least one said discrete skin volume through said at least one first electrode for a predetermined pulse duration $t_1$;

ii. deactivating said at least one of said switches;

iii. waiting a predetermined delay time $t_2$; and, iv. repeating steps (i)-(iii) until said treatment is complete wherein: (a) the distance between said first and second electrode is maximized; (b) said pulse duration $t_1$ is in a range from about 5 ms to about 30 ms; (c) said delay time $t_2$ is in a range from about 1 ms to about 30 ms, further wherein said connector comprises flexible material and said contactor and said electrode comprise stiff material;

thereby applying at least a portion of said energy to said at least one skin volume via said electrical connection.

It is another object of the present invention to disclose the method, additionally comprising at least one of the following steps:

a. selecting $t_2$ to be about 2 ms; and b. selecting the distance between at least one first electrode being activated and at least one second electrode being activated to be a maximum.

It is another object of the present invention to disclose the method, additionally comprising step of selecting said connector having spring-like properties.

It is another object of the present invention to disclose the method, additionally comprising step of providing electrical connection between said at least one switching module, said at least one energy generator and at least one said connector by means of a PCB.

It is another object of the present invention to disclose the method, additionally comprising step of reversibly electrically connecting said treatment tip to said switching module.

It is another object of the present invention to disclose the method, additionally comprising at least one of the following steps:

a. providing said contactor having substantially the shape of a cylinder characterized by a main longitudinal axis;

b. selecting the material of said contactor from a group consisting of copper alloy, steel, gold alloy, conductive polymer and any combination thereof;

c. comprising said contactor of stainless steel;

d. selecting the material of said electrode from a group consisting of stainless steel, copper alloy, gold alloy, conductive polymers and any combination thereof; and e. comprising said electrode of stainless steel.

It is another object of the present invention to disclose the method, additionally comprising step of physically contacting said contactor with said electrode on at least a portion of a side parallel to said main longitudinal axis.

It is another object of the present invention to disclose the method, additionally comprising step of selecting the ratio A/B to be in a predetermined range, said predetermined range being from about 0.9 to about 0.995.

It is another object of the present invention to disclose the method, additionally comprising step of selecting said treatment to be RF treatment.

It is another object of the present invention to disclose the method, additionally comprising step of applying said energy across an applied voltage, said voltage being in at least one of the following ranges: about 160 V to about 320 V RMS; about 180 V to about 300 V RMS; and about 220 V to about 280 V RMS.

It is another object of the present invention to disclose the method, additionally comprising step of cutting through the stratum corneum.

It is another object of the present invention to disclose the method, additionally comprising steps of: selecting said at least one discrete skin volume to be tissue located beneath said skin; selecting said at least one discrete skin volume to be tissue located beneath the stratum corneum of said skin.

It is another object of the present invention to disclose the method, additionally comprising step of providing at least one control unit and regulating the application of said energy by means of the same.

It is another object of the present invention to disclose the method, additionally comprising step of monitoring physical tissue parameters and changing said applied energy accordingly.

It is another object of the present invention to disclose the method, additionally comprising step of simultaneously connecting M electrodes to said energy generator via at least one said switch, where M is an integer in the range from 1 to N.

It is another object of the present invention to disclose the method, additionally comprising step of selecting the range for the ratio M/N from a group consisting of: 1/N to about 10%; about 10% to about 25%, and greater than about 25%.

It is another object of the present invention to disclose the method, additionally comprising at least one of the following steps:

a. selecting N to be about 40;

b. providing each said electrode with between about 1 and about 5 said protruding conducting elements;

c. providing each said electrode with 4 said protruding conducting elements;

d. selecting the distance between said protruding conducting elements to be about 1 mm; and e. selecting the density of said protruding conducting elements to be about 120 per $cm^2$.

It is another object of the present invention to disclose the method, additionally comprising step of selecting the shape of said protruding conducting element to be substantially a prism characterized by a rectangular base of length L and width W, two four-sided side faces of length L, and two three-sided end faces of said height A, said hypotenuse B and width W, said base conjoined with said electrode.

It is another object of the present invention to disclose the method, additionally comprising at least one of the following steps:
a. selecting said length L to be in a range of about 25 μm to about 500 μm;
b. selecting said length L to be about 150 μm;
c. selecting said angle θ to be in a range of about 10° to about 50°;
d. selecting said angle θ to be about 30'; and
e. selecting the shape of said side faces of said triangular prism from a group consisting of flat, inwardly curving, outwardly curving and any combination thereof.

It is another object of the present invention to disclose the method, additionally comprising step of providing a mechanism for cooling at least a portion of said skin, said cooling mechanism selected from a group consisting of: applying a pre-cooled liquid directly to said skin; applying a pre-cooled liquid to said skin via tubes within said applicator, said tubes contacting said skin; applying a pre-cooled spray to said skin; applying a cryogenic spray to said skin; applying a thermo-electric contact cooler to said skin and any combination thereof.

It is another object of the present invention to disclose the method, additionally comprising at least one of the following steps:
a. disposing of said treatment tip;
b. reusing said applicator;
and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PREFERRED EMBODIMENTS

Figure 1:
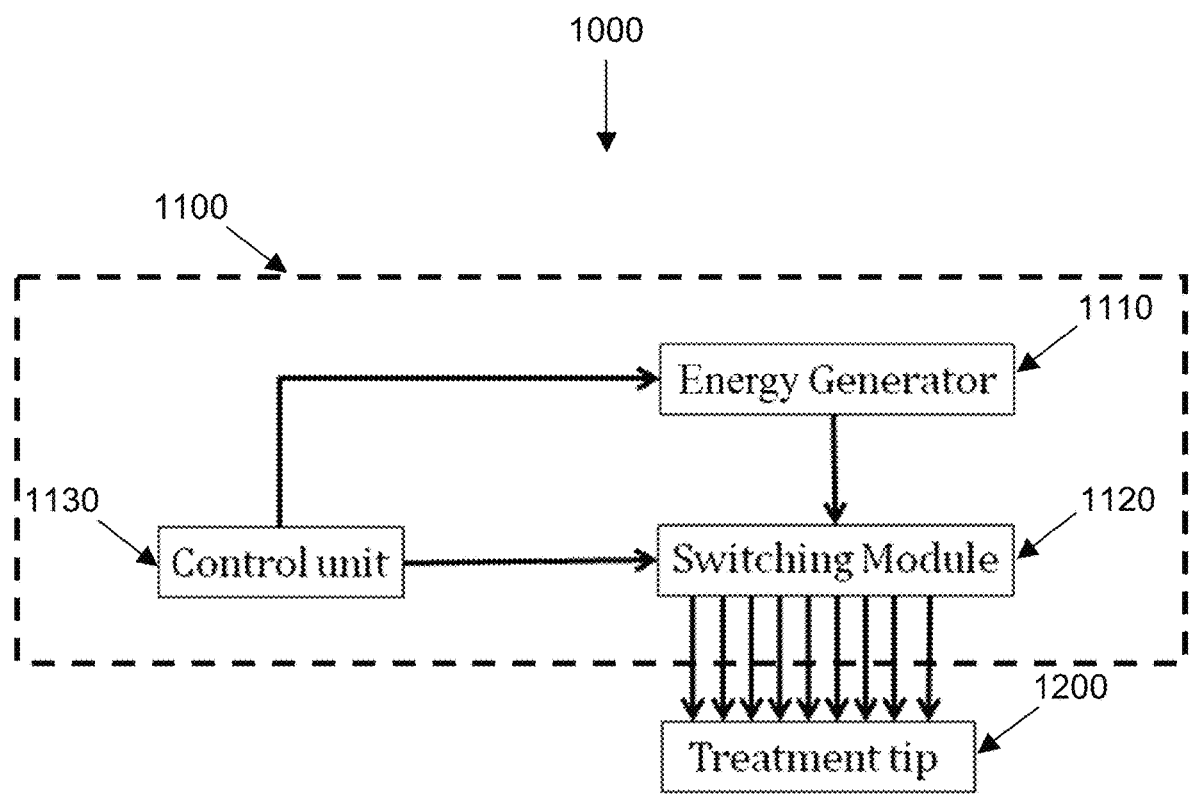
FIG. 1 shows a schematic of the principal parts of the device.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for treating skin by application of energy to the skin to cause heating, coagulation or resurfacing of the skin. The energy can be RF energy, any electrical current, and any combination thereof.

The term 'Radio Frequency (RF)' hereinafter refers in a non-limiting manner to part of the electromagnetic spectrum with frequency in the range of about 50 kHz to about 10 MHz.

The term 'treatment' hereinafter refers to a self-contained procedure wherein energy is applied in a predetermined manner to a predetermined region of the skin. Typically, the predetermined region of the skin is defined by the area of the treatment tip. Treatment can be applied to the skin surface, to tissues below the skin surface, or any combination thereof. Typically, the predetermined manner is a sequence of predefined steps. During any given step, energy can be applied to the entire predetermined region, or to one or more portions of the region, or no energy can be applied, and combinations thereof. Preferably, each step will consist of a predefined time during which energy is applied, followed by a predefined time during which no energy is applied. After completion of the treatment, a region of the skin can be untreated, with no energy having been applied to it; treated during only one step; or treated a during a plurality of steps. Portions of the skin can be left untreated or treated only during a fraction of the steps in order to reduce pain. For example, the applicator can be designed so that treated volumes of skin are physically separated so that each treated volume is surrounded on all sides by untreated skin.

The term 'pulse' hereinafter refers to the period of time within a single step during which energy is applied to at least one region of the skin.

The terms 'fractional RF' and 'fractional RF treatment' hereinafter refer to treatments in which, at any step, the RF energy is applied only to a fraction of a predetermined skin region, preferably, a small fraction of the predetermined skin region.

The term 'collagen' hereinafter refers in a non-limiting manner to a long, fibrous structural protein which is a major component of the extracellular matrix that supports most tissues and gives cells structure. It is responsible for skin strength and elasticity, and its degradation leads to wrinkles that accompany aging.

The term 'epidermis' hereinafter refers in a non-limiting manner to the outermost layer of the skin.

The term 'stratum corneum' hereinafter refers to the upper non-conductive layer of the epidermis.

The term 'dermis' hereinafter refers in a non-limiting manner to a layer of skin beneath the epidermis that consists of connective tissue, and cushions the body from stress and strain.

The term 'about' hereinafter refers to a range of 25% below or above a quoted value.

The terms 'specific absorption rate' and 'SAR' hereinafter refer to a measure of the rate at which energy is absorbed by the human body when exposed to energy, especially the energy of a radio frequency (RF) electromagnetic field. It is defined as the power absorbed per unit mass of tissue and has units of watts per kilogram (W/kg).

The term 'protruding conducting element' hereinafter refers to a portion of the distal end of an electrode which is configured to penetrate the skin.

The term 'contactor' hereinafter refers to a portion of the applicator which provides individual electrical connection between at least one switch and at least one electrode.

The term 'electrode contact' hereinafter refers to a portion of the proximal end of an electrode. Each electrode contact is in physical contact with a contactor, and provides individual electrical connection between at least one switch and the electrode.

The term 'connector' hereinafter refers to a flexible, preferably spring-like, component which provides electrical connection between a switch and a contactor. Typically, there is one connector per contactor. Typically, a switch is electrically connected to an electrode via at least one connector, at least one contactor and at least one electrode contact. The connector ensures that the physical (mechanical) connection between a switch and an electrode is flexible and also ensures that there is a good electrical connection between the switch and the electrode.

The term 'active electrode' hereinafter refers to an electrode during the time it is delivering current. At all other times, it will be an inactive electrode.

The term 'PCB' hereinafter refers to a printed circuit board mechanically supporting and electrically connecting electronic components using conductive tracks, pads and other features etched from copper sheets laminated onto a non-conductive substrate. In typical embodiments of the present device, components such as, but not limited to, switches and energy generators are mechanically supported by the PCB and electrically connected to each other and to other components such as, but not limited to, connectors via the PCB.

In the present invention, which seeks to provide an improved apparatus and improved methods for treating skin, the energy is preferably applied to very small area (less than 10% of the treatment tip) and this active area is scanned across the treatment tip area during a single treatment, thereby providing RF treatment to a fraction of the skin, as is described more in detail hereinbelow.

In some embodiments, the energy can be provided to larger areas of the skin.

The area scanned during a single pulse can consist of a single active electrode or a few electrodes. If only small amounts of energy are delivered to the tissue during a pulse, the pain will be small. Different patterns of active electrodes can be used. For example, the pattern can be that, given a set of electrodes activated during a given pulse, the set of electrodes activated during the next pulse will be those furthest from the previously activated electrodes. This method decreases the sensation of pain even more.

Since electrical current is delivered through one electrode or a small group of electrodes, the homogeneity of the current delivered to the active electrodes is high and therefore the delivered energy distribution is equal across the tip of any given electrode and is substantially the same across all of the active electrodes.

Having the ability to create a device configured to deliver energy in a predeterminable pattern can adapt the treatment area to the area of a lesion. For example, for treatment of a long and narrow wrinkle or a stretch mark, the part of the treatment tip covering the lesion can be activated or a predefined energy distribution along the target can be created.

Different types, shapes and sizes of treatment tip can be used with the device. Since the same effective total treatment tip area is activated at any given time, even though the treatment tip size or shape has been changed the total impedance seen by the device remains constant and the effectiveness of the device is substantially unaffected by the treatment tip change.

Prior art devices typically comprise an energy generator connected to the treatment tip, so that all electrodes in the treatment tip are activated simultaneously. In order to achieve the advantages disclosed hereinabove, an additional component is needed in the device. The current invention utilizes a switching module between the energy generator and the treatment tip. The role of the switching module is to switch the electrical current from electrode to electrode sequentially, so as to provide fractional RF treatment to the skin.

The current device comprises a reusable handle, the applicator, reversibly attachable to a disposable treatment tip, with the applicator comprising the electronics and the treatment tip comprising the electrodes.

FIG. 1 shows a schematic (1000) of the principal parts of an embodiment of the device. In this embodiment, the device comprises a reusable handheld applicator (1100) and a disposable treatment tip (1200), comprising electrodes (not shown) and protruding conducting elements (not shown). The handheld applicator (1100) comprises an energy generator (1110) to generate the energy to be applied to the skin tissue and a switching module (1120) to control transfer of energy to the skin tissue, so as to provide fractional RF treatment of the skin. The energy generator (1110) and switching module (1120) are controlled by a control unit (1130).

The energy generator (1110) produces RF energy, which can be applied to a skin volume as an AC voltage and current via the protruding conducting elements, Current is delivered to the switching module (1120), which can switch the voltage and current in a predefined sequence to the different electrodes to provide the fractional RF treatment. The control unit (1130) controls the sequence of switching, namely, the order in which switches are closed and opened; the pulse duration, the time at least one switch is closed and energy is suppliable to a skin volume; and the delay time, the time where no switches are closed and no energy is applied to the skin volume.

Also controllable by the control unit (1130) are the frequency of the energy; there can be many frequencies of the energy in any one pulse and the frequency and delivered energy can vary during a pulse.

The switching module (1120) and energy generator (1110) can be close to each other or be separated. In close embodiments, the applicator comprises both the switching module (1120) and the energy generator (1110). In separated systems, there is a separate console (not shown) which comprises the energy generator (1110) while the switching module (1120), is in the applicator.

Figure 2:
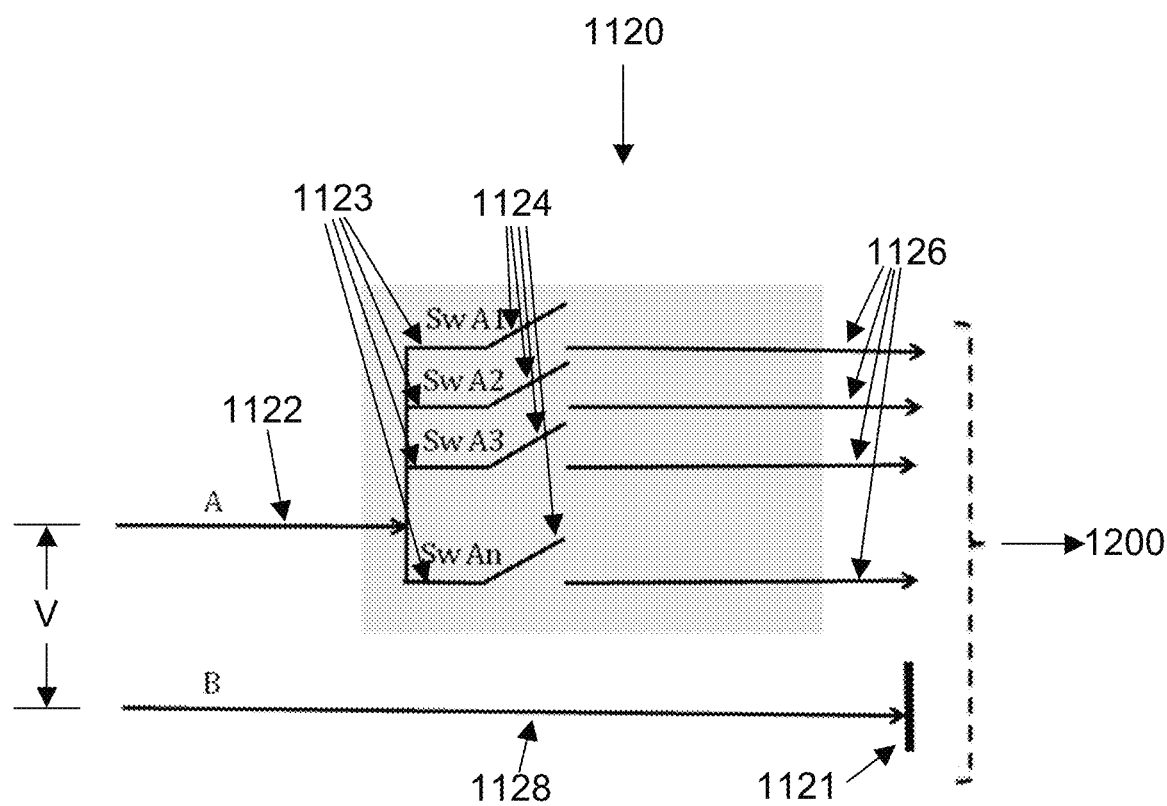
FIGS. 2-4 show schematics of embodiments of the switching module.

FIG. 2 shows a not-preferred embodiment of a switching module (1120) adapted to provide fractional RF treatment by means of current delivered to a skin volume. In this not-preferred embodiment, Line A (1122) from the energy generator is split in the switching module into a plurality of N branches (1123), where N is the number of electrodes in the treatment tip (1200). Each branch comprises an On/Off switch (Sw A1, ..., An), 1124). During at least a portion of the treatment, at least one of the switches is closed so that current flows to at least one electrode, while the remainder are open. The electrical current passes through the closed switch (or switches) and through an electrode (not shown) and protruding conducting element (not shown) in the treatment tip (1200) and returns through tissue (not shown and a return electrode (1121) to Line B (1128). The return electrode (1121) can be part of the treatment tip (1200) or it can be a separate pad connected to the patient's body. In some variants of the not-preferred embodiment, the return electrode (1121) comprises at least one protruding conducting element; in other variants the return electrode (1121) does not comprise a protruding conducting element and contacts the surface of the skin only.

The voltage V applied to the body can be measured across Lines A (1122) and B (1128).

Figure 3:
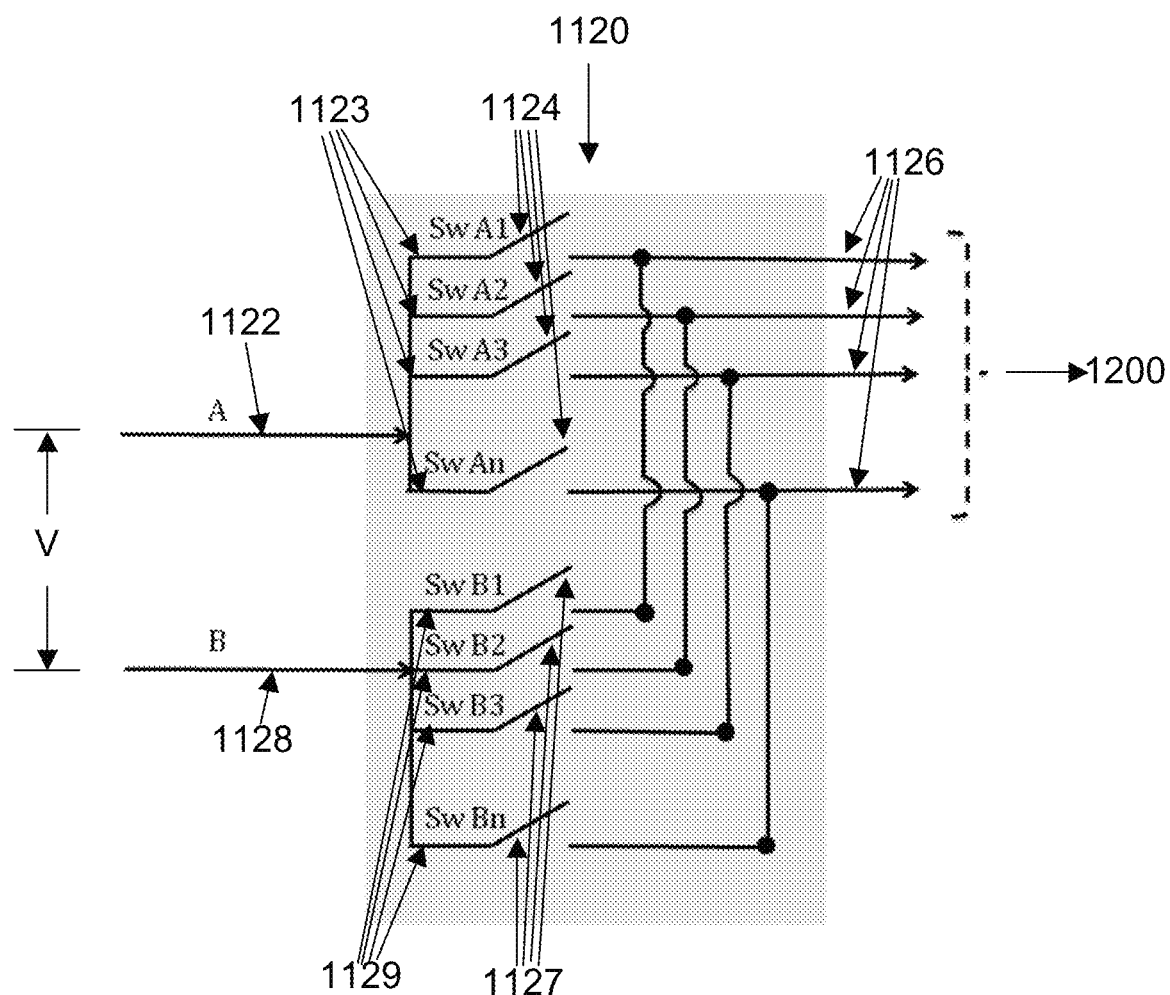

FIG. 3 shows another embodiment of a switching module (1120) adapted to provide fractional RF treatment by means of a current delivered to a skin volume. In this embodiment, at least one of the electrodes (preferably a minority thereof) is active (delivers current through the at least one electrode (not shown) and at least one protruding conducting element (not shown) into the tissue (not shown)) and the rest of the electrodes (preferably a majority thereof) form a return path. Lines A (1122) and B (1128) come from the energy generator. Each line splits into a plurality of N parallel branches (1123, 1129) where N is the number of electrodes in the treatment tip (1200). Each branch includes an On/Off switch (Sw A1, . . . , An, 1124; Sw B1, . . . , Bn, 1127) which can reversibly connect one branch of Line A (1123), and one branch of Line B (1129) to an electrode in the treatment tip (1200). During treatment, at least one of the switches A1, . . . , An (1124) in Line A (1122) can be closed; the remainder will be open. For Line B (1128), the switches B1, . . . , Bn, (1127) corresponding to open switches A1, . . . An (1124) in Line A (1122) will be closed, while the switches corresponding to closed switches A1, . . . , An (1124) in Line A (1122) will be open. The electrical current will pass through the closed switches A1, . . . , An, (1124) in Line A (1122) to the treatment tip (1200) and return back through closed switches B1, . . . , Bn, (1127) in Line B (1128).

The embodiment of FIG. 3 allows work without a return electrode but requires twice as many switches as the not-preferred embodiment shown in FIG. 1.

Figure 4:
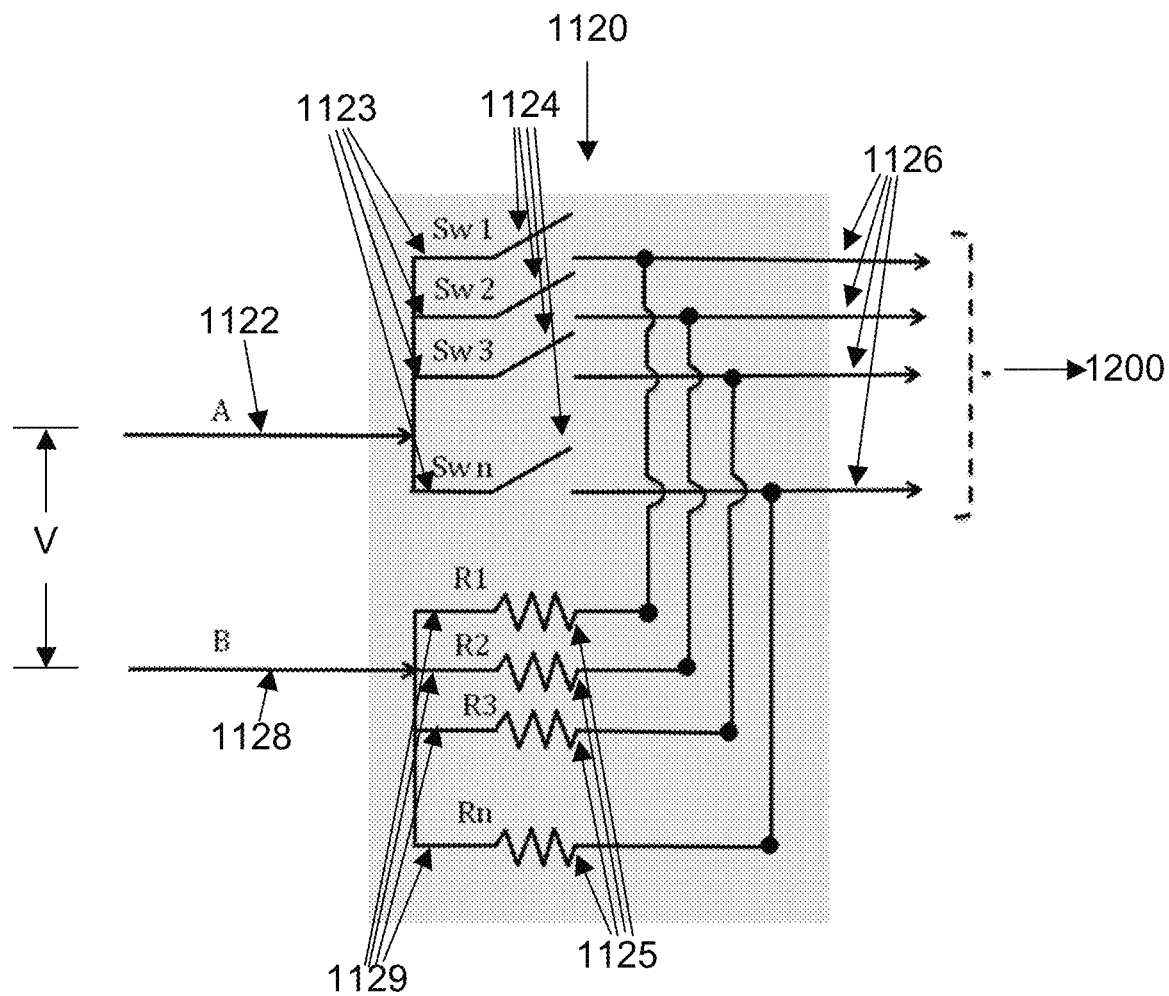

FIG. 4 shows another embodiment of a switching module (1120) adapted to provide fractional RF treatment by means of a current delivered to a skin volume. In this embodiment, as in the embodiment of FIG. 3, Lines A (1122) and B (1128) come from the energy generator. Each line splits into a plurality of N parallel branches (1123, 1129) where N is the number of electrodes in the treatment tip (1200). Branches of Line A include an On/Off switch (Sw A1, . . . , An, 1124) which can reversibly connect one branch of Line A (1123), and one branch of Line B (1129) to an electrode in the treatment tip (1200).

However, in the embodiment of FIG. 4, resistors R1, . . . , Rn (1125) instead of switches B1, . . . , Bn (1127, FIG. 3) connect all the electrodes (not shown) in the treatment tip (1200) via the branches (1129) to Line B (1128).

During treatment, at least one of the switches A1, . . . , An (1124) in Line A (1122) can be closed; the remainder will be open. Electrical current will pass through the closed switches A1, . . . , An, (1124) in Line A (1122) to the treatment tip (1200) and return back through the resistors R1, . . . , Rn, (1129) in Line B (1128).

The resistance of these resistors R1, . . . , Rn (1129) should be much greater than the typical impedance of the portion of a patient's skin under a single electrode. If, in Line A (1122), one switch A1, . . . , An (1124) is closed, the electrical current will pass through this switch to the tissue. The alternative path through the resistor will take only a small portion of the current, since the resistance of the resistor is much greater than that of the tissue. The return path is through the remainder of the electrodes (not shown) in the treatment tip (1200) and the remainder of the resistors R1, . . . , Rn (1129). All of the resistors R1, . . . , Rn (1129) are connected in parallel and therefore overall resistance will be low so that energy losses in the resistors R1, . . . , Rn (1129) will be small. The additional advantage of an embodiment of this type is that resistors can function as current limiters, which helps to prevent pain and helps to distribute current homogenously across the electrodes.

Figure 5:
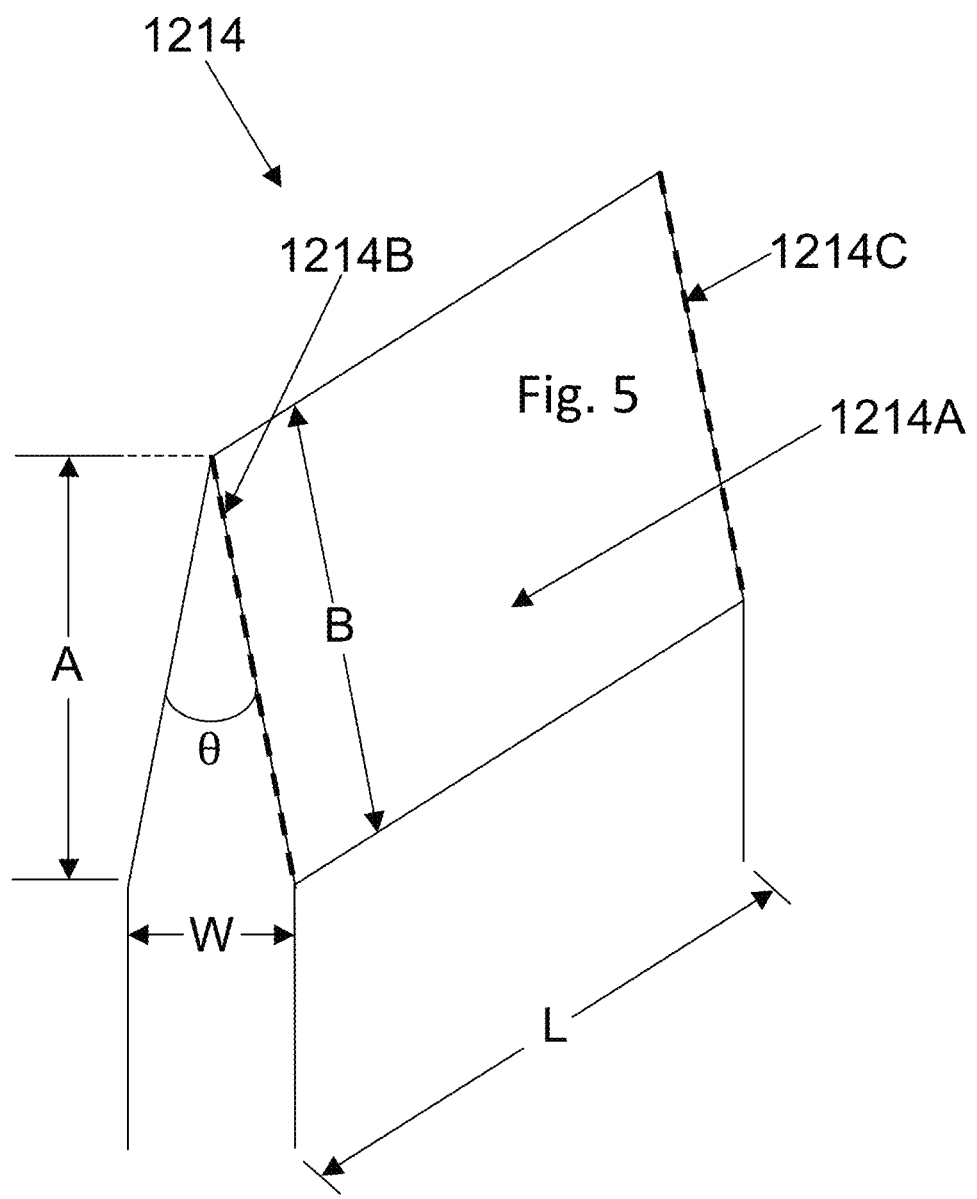
FIG. 5 shows a schematic of an embodiment of the distal end of a protruding conducting element.

FIG. 5 shows a schematic of the distal end of a protruding conducting element (1214); the electrode (1210) to which it is attached is not shown. In this embodiment, the protruding conducting element (1214) forms substantially a triangular prism, with the square base of the prism attached to an electrode (1210, see FIGS. 7 and 8, below). The square base has a length L, typically about 150 µm and a width W. Therefore, the length of the protruding conducting element (1214) and, typically, the electrode (1210), is L, and the width W of the base of the end faces of the prism is about 150 µm.

The angle subtended by the distal end of the end faces, θ, is typically between about 20° and about 50°; preferably, the angle θ is about 30°.

The height A of the end faces is given by $$A = W/(2 \tan(\theta/2))$$

and the length B of the hypotenuse (1214B) of the end faces, the distance between the distal end of the protruding conducting element and the base of the protruding conducting element, is given by $$B = W/(2 \sin(\theta/2))$$

Table 1 shows typical values of θ, A, B and the ratio A/B.

TABLE 1

A, B, and A/B as a function of angle θ.

| Angle θ | A | B | Ratio A/B |
|---------|-----|-----|-----------|
| 20° | 567 | 576 | 0.98 |
| 30° | 373 | 387 | 0.96 |
| 50° | 214 | 230 | 0.93 |

The ratio A/B will be between 0.9 and 0.995 in embodiments of the device; in preferred embodiments, it is about 0.96.

In the schematic shown in FIG. 5, the side faces (1214A) are flat and each hypotenuse (1214B) is collinear with an edge (1214C) of an end face.

However, as shown in FIG. 6A-D, the side faces (1214A) of the prism need not be flat; the edges (1214C) of the side faces (1214A) need not be straight lines and, therefore, the edges (1214C) of the side faces (1214A) need not have the same length as the hypotenuse (length B, 1214B, dashed line).

Figure 6:
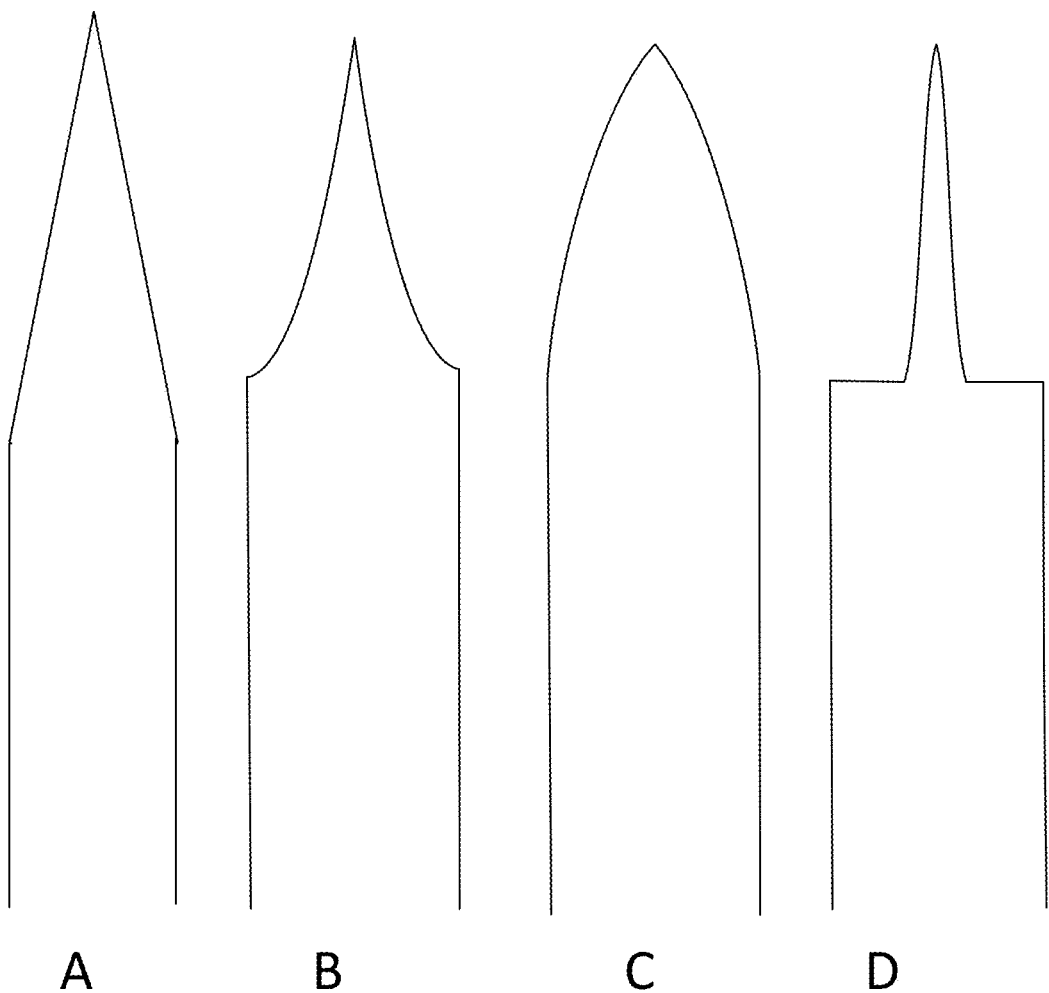
FIG. 6 shows schematics of cross-sections of embodiments of protruding conducting elements.

FIG. 6A-D shows cross-sections of non-limiting exemplary embodiments of protruding conducting elements. FIG. 6A shows a triangular protruding conducting element like that in FIG. 5, while FIG. 6B shows an arcuate protruding conducting element in which the sides faces are curved inward, FIG. 6C shows an arcuate protruding conducting element in which the sides faces are curved outward, and FIG. 6D shows a narrow triangular protruding conducting element with side faces curving outward at the distal end of the protruding conducting element and inward at the proximal end of the protruding conducting element.

In general, the narrower the tip of the distal end of the protruding conducting element and the more slowly the protruding conducting element widens toward its proximal end, the less pain during penetration of the protruding conducting element into the skin, but the more blunting of the distal end of the protruding conducting element during use. On the other hand, the wider the tip of the distal end of the protruding conducting element and the more rapidly the protruding conducting element widens toward its proximal end, the more pain during use, but the longer the protruding conducting element will last.

It has been found that a protruding conducting element angle θ (see FIG. 5, hereinabove) of about 30°, as described hereinabove, is a good compromise between perceived pain and protruding conducting element durability and that protruding conducting element angles θ in the range of 20°-50° provide an acceptable compromise between perceived pain and protruding conducting element durability.

Figure 7:
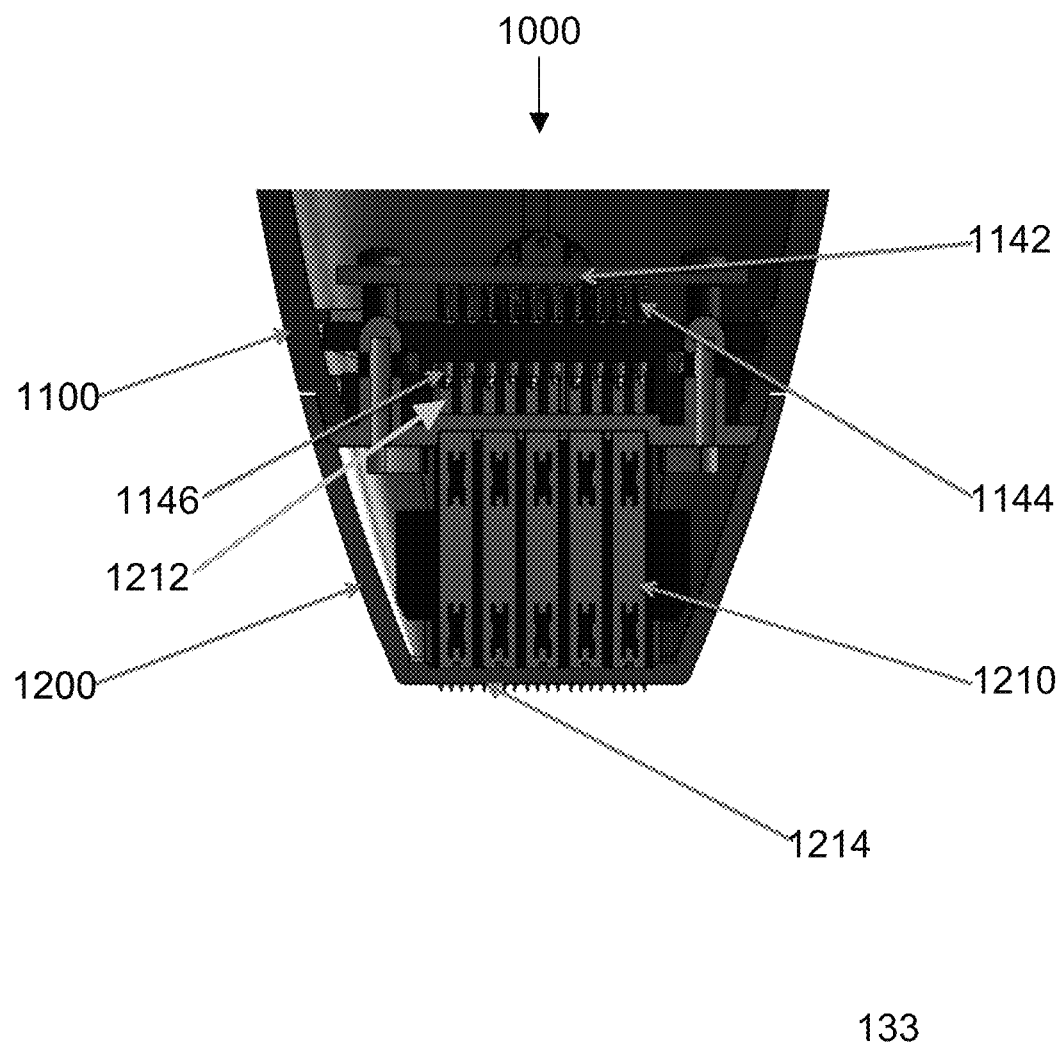
FIG. 7 shows a schematic of the distal end of an embodiment of the applicator.
Figure 8:
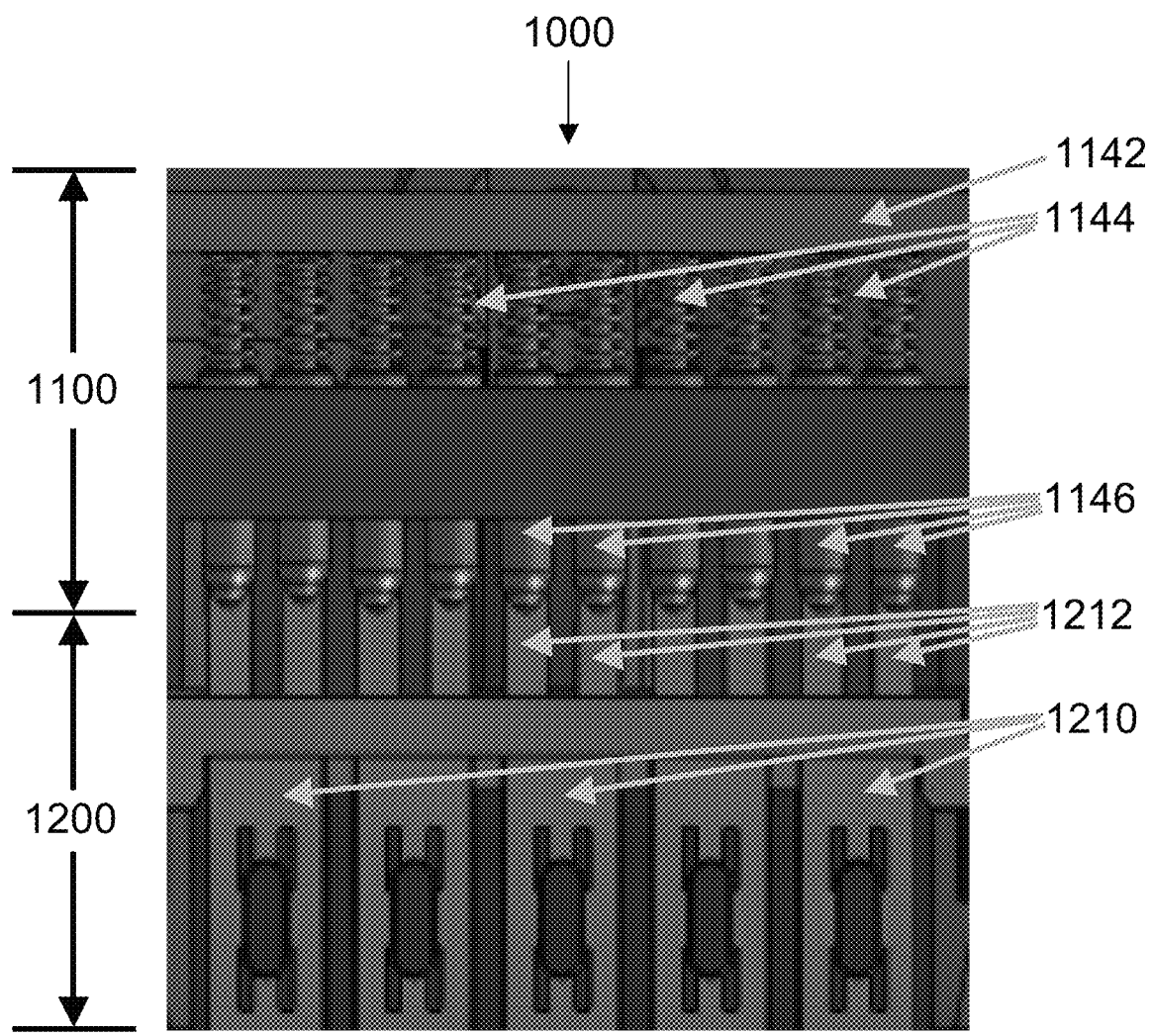
FIG. 8 shows a schematic of an enlarged view of the embodiment of the applicator of FIG. 7.

FIG. 7 shows an embodiment of the device (1000), showing the distal end of the reusable handheld applicator (1100) and the disposable treatment tip (1200), while FIG. 8 shows a close-up of the region of the device (1000) comprising the contacts (1146, 1212). The distal end of the reusable handheld applicator (1100) is shown in the upper part of FIG. 8 and the proximal end of the disposable treatment tip (1200) is shown in the lower part of FIG. 8.

The handheld applicator (1100) comprises a PCB (1142). Typically, the switching module (1120, FIGS. 1-4, hereinabove), the control unit (1130, FIG. 1, hereinabove), and the energy generator (1110, FIG. 1, hereinabove) are mounted on the PCB (1142), with tracks on the PCB (1142) providing electrical connection between the switching module (1120, FIGS. 1-4, hereinabove), the control unit (1130, FIG. 1, hereinabove), and the energy generator (1110, FIG. 1, hereinabove). In FIG. 8, the PCB (1142) is near the upper edge of the figure.

The applicator also comprises at least one connector (1144) and at least one contactor (1146), in electrical connection with the switching module (1120, FIGS. 1-4, hereinabove). As disclosed hereinbelow, connectors (1144) and contactors (1146) form part of a connection mechanism providing electrical connection between switches (1124, not shown) in the applicator (1100) and electrodes (1126, not shown) in the treatment tip (1200).

In some embodiments, at least part of the energy generator (1110, FIG. 1, hereinabove) comprises a separate unit. For non-limiting example, power for the energy generator can be mains power, supplied wiredly from a wall socket. In another non-limiting example, the energy generator forms a separate unit, wiredly connectable to the applicator.

The treatment tip (1200) is reversibly connectable to the applicator (1100). Typically, electrical connection is provided via physical contact between the contactors (1146) in the applicator and electrode contacts (1212) at the proximal end of the electrodes (1210) in the treatment tip (1200).

Each contactor (1146) typically comprises a pin attached to the applicator (1100). In various embodiments, a small amount of movement of the contactor (1146) is possible, the contactor (1146) is flexible, and any combination thereof.

In less-preferred embodiments, the contactor (1146) can comprise a flexible and movable pad attached to the applicator (1100).

The attachment of the contactors (1146) to the applicator (1100) ensures that the treatment tip (1200) can be reliably connected to the applicator (1100) and that, after connection of the treatment tip to the applicator to the treatment tip, the contactors (1146) and the electrode contacts (1212) will be either touching each other or in close physical proximity to each other.

In preferred embodiments, contactors (1146) are comprised of stainless steel because they contact the stainless steel proximal end of the electrode contact (1212) in the disposable tip, and the material of the contactor should be at least as hard as the material in the disposable tip which it is contacting.

In prior-art skin treatment devices with detachable treatment tip, the contactor in the applicator is copper or other high-conductivity material, while the contact in the treatment tip, like the electrode contact of the present device (1212, FIG. 7, hereinbelow) is of stainless steel.

In prior-art devices, copper contacts were used in the applicator because it is almost impossible to weld stainless steel to the PCB, making it almost impossible to have, in the applicator, good electrical connection between the PCB and a stainless steel contact. Therefore, in the prior art devices, because of the flexibility of the contact in the applicator and the stiffness of the contact in the treatment tip, maintaining reasonable electrical connection between the contactors in the applicator and the contacts in the treatment tip was problematic.

In the present invention, both the contactors (1146) and electrode contacts (1212) are of the same material, preferably stainless steel, ensuring good electrical connection between the contactors (1146) and the electrode contacts (1212), while good electrical connection between the contactors (1146) and the PCB (1142) is provided for by connectors (1144), preferably spring-like connectors.

In the embodiment of FIGS. 7 and 8, the connectors (1144) are coil springs. Connectors (1144) such as springs provide for good electrical connection between the contactors (1146) and the PCB (1142).

In the embodiment shown in FIGS. 7 and 8, electrical connection between the PCB (1142) and the contactors (1146) (and therefore the electrodes (1210)) is via the connectors (1144), which are firmly attached at their proximal ends to electrical contacts on the PCB (1142) and are firmly attached at their distal ends to the side of the contactors (1146).

In the embodiment shown in FIGS. 7 and 8, the connectors (1144) comprise a spiral spring, with the proximal portion of the contactors (1146) enclosed within the bore of the spring, thus maintaining the alignment of the contactors (1146) with respect to the electrodes (1146) and also ensuring that there is continuing good-quality electrical contact between the PCB (1142) and the electrodes (1210).

Springs can be leaf springs, coil springs, or any other form of spring known in the art. Preferably, the springs are coil springs, as shown in FIGS. 7 and 8.

Springs can be of any material with high strength, a high elastic limit, a low Young's modulus and a wide elastic range. Springs can comprise iron, copper, tin, aluminum, vanadium, beryllium, nickel, chromium, plastic and any combination thereof. Exemplary spring materials include, but are not limited to, high carbon steel, alloy steel, stainless steel, phosphor bronze, beryllium copper, Monel, and Inconel. In preferred embodiments, the springs are of stainless steel.

In this embodiment, the disposable treatment tip (1200) comprises electrodes (1210) with protruding conducting elements (1214) at their distal end. The electrodes (1210) are in electrical communication with electrode contacts (1212). In preferred embodiments, such as that shown FIGS. 7 and 8, each electrode (1210) forms a single part which comprises at least one electrode contact (1212) at its proximal end and at least one protruding conducting element (1214) at its distal end.

In preferred variants of the electrode, (1210) each electrode (1210) comprises two electrode contacts (1212).

In preferred embodiments, the electrodes (1210), electrode contacts (1212) and protruding conducting elements (1214) are comprised of stainless steel, but any material with good conductivity can be used, for non-limiting example, copper, gold, alloys thereof, conductive polymers and any combination thereof.

Stainless steel is preferably used for the electrodes because of its strength and biocompatibility, which are required for the protruding conducting elements.

In preferred embodiments, such as that shown in FIGS. 7 and 8, each electrode (1210) has four protruding conducting elements (1214), although the number of protruding conducting elements (1214) can range from about 1 to about 4.

In this preferred embodiment, each electrode (1210) has two electrode contacts (1212), with each electrode contact (1212) in electrical communication with one contactor (1146), so that there are twice as many electrode contacts (1212), contactors (1146) and connectors (1144) as there are electrodes (1210).

Figure 9:
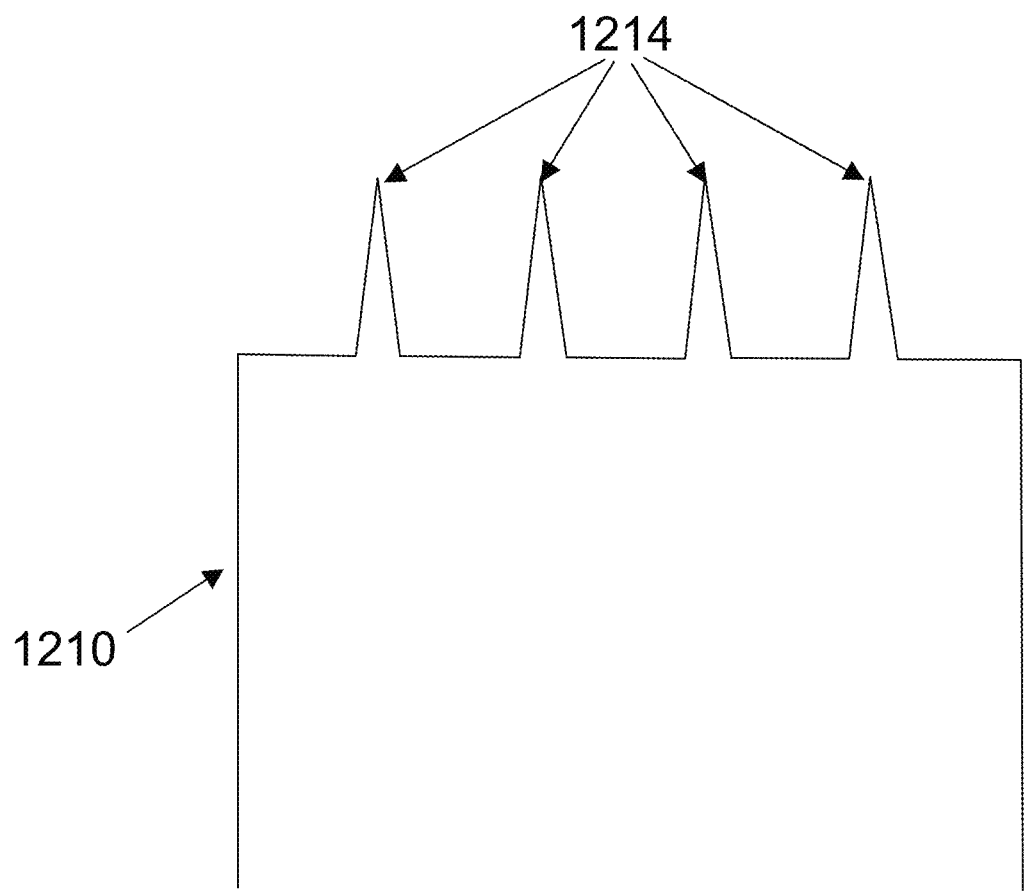
FIG. 9 shows a schematic of an embodiment of the distal end of an electrode.

FIG. 9 shows a schematic of the distal portion of an exemplary electrode (1210) with four protruding conducting elements (1214) at its distal end. In the embodiment of FIG. 9, the protruding conducting elements have triangular end faces and flat side faces. In other embodiments, the side faces can curve inward (FIG. 6B, hereinabove), can curve outward (FIG. 6C, hereinabove), can curve both inward and outward (FIG. 6D, hereinabove), and any combination thereof.

In some embodiments, fractional RF treatment is applied by having the RF pulse applied to a plurality of electrodes; preferably, subsequent pulses are applied to a different plurality of electrodes so as to limit heating of the tissue and minimize pain to the subject.

In preferred embodiments, fractional RF treatment is applied by having each RF pulse applied to a single electrode.

Fractional RF treatments can comprise:
1. each electrode excited once during a treatment (preferred);
2. all electrodes excited, some excited more than once;
3. not all electrodes excited; if an electrode is excited, it is excited once; and
4. not all electrodes excited, some electrodes excited more than once.

In preferred variants of the above embodiments, the electrodes excited in one pulse are at a position as physically distant as is practicable from the electrodes excited in the previous pulse, so as to minimize further RF heating in a volume of tissue already heated by a previous pulse. By this means, overheating of tissue is prevented and pain is minimized.

Figure 10:
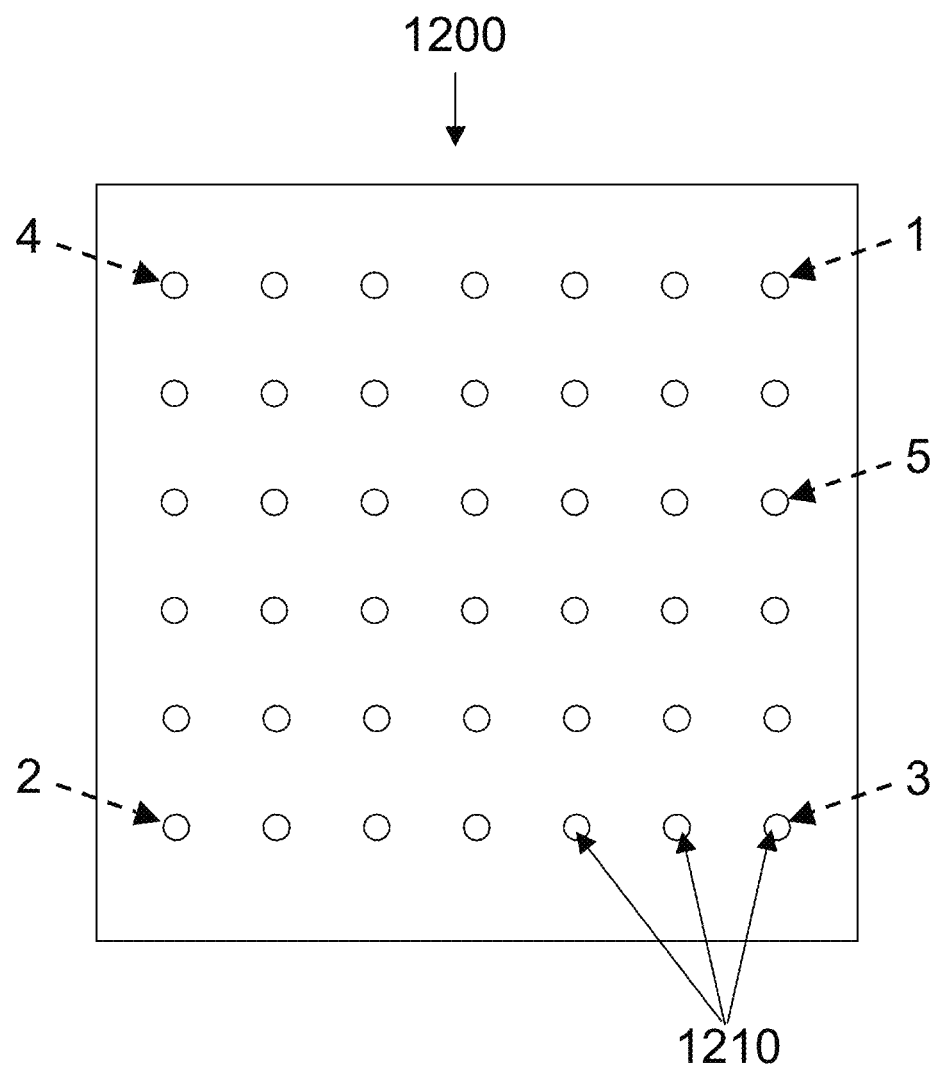
FIG. 10 shows a schematic of a portion of an exemplary sequence of excitations of electrodes in the applicator.

A non-limiting schematic example of a portion of a fractional RF treatment comprising a sequence of excitations in a square array of electrodes is given in FIG. 10. The distal end of a treatment tip (1200) is shown, comprising 42 electrodes (1210) in a 6×7 array. In this example, the first electrode excited (1, dashed arrow) is at the top right of the array. The second electrode excited (2, dashed arrow) is at the bottom left. The third electrode (3, dashed arrow) is at bottom right, and the fourth (4, dashed arrow) at top left. This is followed by the right-most electrode in the third (upper middle) row (5, dashed arrow). The next in the sequence (not shown) would be the left-most electrode in the fourth (lower middle) row, and so on.

Furthermore the system reduces side effects and/or harmful effects of the electromagnetic pulses and/or the deep tissue diathermy such that the reduction of side effects and/or said harmful effects is greater than the sum of the reduction due to the electromagnetic pulses and/or the reduction due to the deep tissue diathermy.

The surface of the skin can be pre-cooled and/or cooled during treatment to avoid damage to the skin in the area between protruding conducting elements.

Skin cooling can be provided by contact cooling, by applying a pre-cooled liquid or cryogen spray directly to the skin and any combination thereof.

Contact cooling can be by means of a cooling mechanism in the applicator, which will also ensure a more uniform heat distribution in the electrodes in the region of the protruding conducting elements. Contact cooling by means of a cooling mechanism in the applicator can be achieved by circulating a cooling fluid through tubes in the applicator.

Contact cooling can be by means of a pre-cooled liquid applied directly to the skin; a pre-cooled liquid applied to the skin via tubes within the applicator, the tubes contacting the skin; a thermo-electric contact cooler and any combination thereof.

Example 1

An embodiment of the device has a disposable treatment tip with 160 protruding conducting elements contacting tissue. The protruding conducting elements are divided to 40 groups of 4 protruding conducting elements each. Each group of 4 protruding conducting elements is connected to one electrode in the device (FIG. 9). The device applies RF energy to one electrode (one group of 4 protruding conducting elements) at a time.

In this embodiment, the total energy delivered to each protruding conducting element can be up to 62 mJ, with the total energy in one application (comprising sequential application to all 160 protruding conducting elements) can be up to 9.92 J.

In this embodiment, the distance between protruding conducting elements is 1 mm and the density of the protruding conducting elements is 120 protruding conducting elements/cm$^2$.

Each protruding conducting element has the shape of micro-knife (see FIG. 6A, hereinabove), with the angle subtended by the distal end of the micro-knife being 30°. The area of contact of each protruding conducting element is 20 μm×150 μm. During application of the device (by applied pressure), the protruding conducting elements cut through the stratum corneum and penetrate to lower layers of the skin, which conduct RF electrical current well. Then, when the RF energy is applied, the device ablates tissue, so that the protruding conducting elements penetrate further into the tissue. Recent studies demonstrate that the maximum penetration can be up to 600 μm.

In preferred embodiments, the depth of penetration is between 200 μm and 500 μm.

Energy delivery to the protruding conducting elements is controlled by means of two parameters: RMS voltage of the RF energy (between about 220 V and 280 V) and pulse duration (between about 5 ms and about 30 ms).

The sensation of pain was decreased by regulating the separation in time of the pulses (about 15 ms between pulses).

In the foregoing description, embodiments of the invention, including preferred embodiments, have been presented for the purpose of illustration and description. They are not intended to be exhaustive or to limit the invention to the precise form disclosed. Obvious modifications, variations and combinations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system for treating the skin by heating at least one discrete skin volume, comprising:
 a. at least one treatment tip, said treatment tip being disposable, comprising N electrodes, N being an integer in a range between 2 and 42 inclusive; each of said N electrodes having at least two protruding conducting elements;
  at least one of said at least two protruding conducting elements is configured to penetrate the skin surface at least one discrete location; at least one of said N electrodes is configured to apply energy to said at least one discrete skin volume so as to heat said at least one discrete skin volume;
 b. an energy generator configured to generate energy to be applied to the skin tissue;
 c. at least one switching module adapted to control transfer of energy to at least one of said N electrodes, so as to provide fractional RF treatment of the skin, and
 d. a control unit to control transfer of energy to the skin tissue by control of the energy generator and the at least one switching module;
 wherein said at least one switching module comprises a first line, a return line, N switches and N resistors,
 said first line and said return line electrically connectable to said energy generator; and for each pth switch, $1<p<N$,
  said pth switch is electrically connected on a first side to said first line; said pth switch is electrically connected on a second side to a pth resistor and, said treatment tip being connected to said applicator, electrically connected to a pth electrode;
  said pth switch is configured, when open, to enable passage of electric current from said energy generator through said first line and through said switch to said pth electrode, and from said pth electrode through said return line to said energy generator; and said pth switch configured, when closed, to prevent passage of electric current from said energy generator to said pth electrode;
 a resistance of each of said N resistors is configured to generate a return path of current from said pth electrode via all other of said N electrodes, said current being divided between said all other of said N electrodes, distributing said current homogeneously across said all other of said N electrodes and minimizing plan to a user.

2. The system of claim 1, wherein at least one of the following is true:
 a. said treatment is RF treatment;
 b. said energy generator is configured to supply voltage in at least one of the following ranges:
  i. the applied voltage is in a range from 160 V RMS to 320 V RMS;
  ii. the applied voltage is in a range from 180 V RMS to 300 V RMS; and,
  iii. the applied voltage is in a range from 220 V RMS to 280 V RMS;
 c. at least one of said at least two protruding conducting elements is configured to cut through the stratum corneum of said skin;
 d. said at least one discrete skin volume is tissue located beneath said skin;
 e. said at least one discrete skin volume is tissue located beneath the stratum corneum of said skin;
 f. a duration between activation of and deactivation of at least one of said N electrodes is in a range from 5 ms to 30 ms;
 g. a delay time between deactivation of and activation of at least one of said N electrodes is in a range from 1 ms to 30 ms;
 h. a distance between each of said at least two protruding conducting elements and any adjacent one of said at least two protruding conducting elements is 1 mm;
 i. at least one of said at least two protruding conducting elements having cross sectional area selected from a group consisting of: a triangular cross section, an arcuate cross section in which at least one side rib is curved inward, an arcuate cross section in which at least one side rib is curved outward and any combination thereof;
 j. each of said at least two protruding conducting elements is characterized by dimensions of height A, length B of at least one rib and an angle $\theta$ between at least two of said ribs; the ratio A/B is in a predetermined range, said predetermined range being between 0.9 and 0.995; and
 k. each of said at least two protruding conducting elements is characterized by a substantially prism shape tip with rectangular base characterized by having two four-sided faces of length L, said length L being in a range of 25 μm to 500 μm.

3. The system of claim 1, said at least one switching module additionally comprising at least one switch configured to reversibly connect said energy generator to at least one of said N electrodes; wherein said at least one switch is configured to simultaneously connect a number M of said N electrodes to said energy generator; at least one of the following being true:
 a. the ratio M/N is in a range selected from a group consisting of: for N>10, 1/N to 10%; greater than 10% to 25%; and greater than 25%;
 b. N is 40; and,
 c. said system additionally comprises at least one flexible connector, said electrical connection between said at least one switch and at least one of said N electrodes being via said at least one flexible connector, said at least one flexible connector comprises a spring.

4. The system of claim 1, wherein at least one of the following is true:
 a. at least one of said N electrodes comprises between 2 and 5 of said at least one of said at least two protruding conducting elements;
 b. at least one of said N electrodes comprises 4 of said at least one of said at least two protruding conducting elements;
 c. said system additionally comprises a printed circuit board (PCB) configured to provide electrical connection between said at least one switching module, said energy generator and at least one said at least one flexible connector;
 d. said system additionally comprises a mechanism for cooling at least a portion of said skin, said cooling mechanism selected from a group consisting of: a pre-cooled liquid applied directly to said skin; a pre-cooled liquid applied to said skin via tubes within said applicator, said tubes contacting said skin; a pre-cooled spray applied to said skin; a cryogenic spray applied to said skin; a thermo-electric contact cooler and any combination thereof;

e. at least one of said N electrodes is made of material selected from a group consisting of stainless steel, copper, gold, conductive polymers and any combination thereof;

f. at least one of said N electrodes comprises stainless steel;

g. Q second switches connect a number O of said return electrodes to said energy generator, such that electrical current is returned from said M active electrodes to said energy generator through said O return electrodes and Q second switches, thereby said electrical current returned to said energy generator is distributed between all of said O return electrodes; where Q is an integer in the range from 1 to N; O is an integer in the range from 1 to N-M; and h. said system is a close, stand-alone system.

5. The system of claim 1, wherein said protruding conducting element is shaped substantially as a triangular prism characterized by a rectangular base of length L and width W, two four-sided side faces of length L, two four-sided end faces of said length L and hypotenuse B, and two three-sided end faces of said height A, a hypotenuse B and width W, said base conjoined with said electrode; further wherein at least one of the following is being held true:

a. said length L is 150 μm;

b. the angle θ subtended by the distal end of the end faces of the two four-sided end faces of said length L and hypotenuse B is in a range of 10° to 50°;

c. the angle θ subtended by the distal end of the end faces of the two four-sided end faces of said length L and hypotenuse B is 30°; and, d. said side faces of said triangular prism have a shape selected from a group consisting of flat, inwardly curving, outwardly curving and any combination thereof.

6. The system of claim 4, wherein said treatment tip is reversibly electrically connectable to said at least one switching module, said applicator additionally comprising at least one contactor configured to provide said reversible electrical connection between at least one of said N electrodes in said treatment tip and at least one of said at least one switch in said at least one switching module; at least one of the following is being held true:

a. said at least one contactor has substantially the shape of a cylinder characterized by a main longitudinal axis; said at least one contactor is configured to be in physical contact with at least one of said N electrodes on at least a portion of a side parallel to said main longitudinal axis;

b. said at least one contactor is made of material selected from a group consisting of copper, steel, gold, conductive polymer and any combination thereof; and, c. said at least one contactor comprises stainless steel.

7. The system of claim 1, wherein said applicator is reusable.

8. The system of claim 1, wherein said N electrodes are further connected to said energy generator by means of at least one selected from a group consisting of N second switches, N resistors and any combination thereof.

9. A method for reducing pain during skin treatment, comprising steps of:

a. providing a device for treating the skin, comprising:
   i. at least one treatment tip, said treatment tip being disposable, said treatment tip comprising N electrodes, N being an integer in a range between 2 and 42 inclusive, each of said N electrodes having at least two protruding conducting elements; at least one of said at least two protruding conducting elements is configured to penetrate the skin surface at at least one discrete location; at least one of said N electrodes is configured to apply energy to at least one discrete skin volume so as to heat said at least one discrete skin volume;
   ii. an energy generator configured to generate energy to be applied to the skin tissue;
   iii. at least one switching module to control transfer of energy to at least one of said N electrodes, so as to provide fractional RF treatment of the skin; and
   iv. a control unit to control transfer of energy to the skin tissue by control of the energy generator and the at least one switching module;

b. connecting said treatment tip to said applicator;

c. activating said energy generator such that electrical current is suppliable to at least one of said N electrodes; and, d. activating said at least one switching module according to a predetermined sequence:
   i. creating an electrical connection between said energy generator and at least one first electrode, thereby delivering energy to at least one said discrete skin volume through said at least one first electrode for a predetermined pulse duration $t_i$;
   ii. ending said electrical connection between said energy generator and at least one first electrode;
   iii. waiting a predetermined delay time $t_2$; and,
   iv. repeating steps (i)—(iii) until said treatment is complete wherein said method additionally comprising steps of providing said at least one switching module with a first line, a return line, N switches and N resistors, said first line and said return line electrically connectable to said energy generator; and for each pth switch, 1<p<N, said pth switch is electrically connected on a first side to said first line;

said pth switch is electrically connected on a second side to a pth resistor and, said treatment tip being connected to said applicator, electrically connected to a pth electrode;

said pth switch is configured, when open, to enable passage of electric current from said energy generator through said first line through said switch to said pth electrode, and from said pth electrode through said return line to said energy generator; and said pth switch configured, when closed, to prevent passage of electric current from said energy generator to said pth electrode;

a resistance of each of said N resistors is configured to generate a return path of current from a pth electrode via all other of said N electrodes, said current being divided between said all other of said N electrodes, distributing said current homogeneously across said all other of said N electrodes and minimizing pain to a user.

10. The method of claim 9, additionally comprising at least one of the following steps:
   a. providing at least one connector characterized by a proximal end and a distal end, said at least one connector electrically connected at its proximal end to said at least one switching module, electrical connection between said at least one switching module, said energy generator and at least one of said at least one connector by means of a PCB;
   b. providing a mechanism for cooling at least a portion of said skin, said cooling mechanism selected from a group consisting of: applying a pre-cooled liquid directly to said skin; applying a pre-cooled liquid to said skin via tubes within said applicator, said tubes contacting said skin; applying a pre-cooled spray to said skin; applying a cryogenic spray to said skin; applying a thermo-electric contact cooler to said skin and any combination thereof;
   c. reversibly electrically connecting said treatment tip to said at least one switching module;
   d. providing at least one contactor electrically connectable to at least one of said N electrodes, said contactor electrically connected at its distal end to said at least one connector; said at least one contactor having substantially the shape of a cylinder characterized by a main longitudinal axis; and physically contacting said at least one contactor with at least one of said N electrodes on at least a portion of a side parallel to said main longitudinal axis;
   e. selecting the material of said at least one contactor from a group consisting of copper alloy, steel, gold alloy, conductive polymer and any combination thereof;
   f. comprising said at least one contactor of stainless steel;
   g. selecting the material of at least one of said N electrodes from a group consisting of stainless steel, copper alloy, gold alloy, conductive polymers and any combination thereof;
   h. comprising at least one of said N electrodes of stainless steel;
   i. providing Q second switches and connecting a number 0 of said return electrodes to said energy generator, such that electrical current is returned from said M active electrodes to said energy generator through said 0 return electrodes and Q second switches, thereby said electrical current returned to said energy generator is distributed between all of said O return electrodes; where Q is an integer in the range from 1 to N; O is an integer in the range from 1 to N-M;
   j. at least one of said at least two protruding conducting elements having cross sectional area selected from a group consisting of: a triangular cross section, an arcuate cross section in which at least one side rib is curved inward, an arcuate cross section in which at least one side rib is curved outward and any combination thereof;
   k. characterizing each of said at least one of said at least two protruding conducting elements by dimensions of height A, length B of at least one rib and an angle θ between at least two of said ribs; the ratio A/B is in a predetermined range, said predetermined range being between 0.9 and 0.995;
   l. characterizing each of said at least two protruding conducting elements by a substantially prism shape tip with rectangular base characterized by having two four-sided faces of length L, said length L is in a range of 25 µm to 500 µm; and
   m. said system is a close, stand-alone system.

11. The method of claim 9, additionally comprising at least one of the following steps:
   a. selecting said treatment to be RF treatment;
   b. applying said energy across an applied voltage, said voltage being in at least one of the following ranges: 180 V RMS to 300 V RMS; and 220 V RMS to 280 V RMS;
   c. cutting through the stratum corneum;
   d. selecting said at least one discrete skin volume to be tissue located beneath said skin;
   e. selecting said at least one discrete skin volume to be tissue located beneath the stratum corneum of said skin;
   f. selecting said pulse duration $t_1$ to be in a range from 5 ms to 30 ms;
   g. selecting said delay time $t_2$ to be in a range from 1 ms to 30 ms;
   h. selecting said at least one connector comprising flexible material and said at least one contactor and at least one of said N electrodes comprising stiff material;
   i. selecting said voltage supplied by said energy generator to be in a range from 160 V RMS to 320 V RMS; and
   j. selecting a distance between each of said at least two protruding conducting elements and any adjacent one of said at least two protruding conducting elements to be 1 mm; and selecting said at least one connector comprising a spring.

12. The method of claim 9, additionally comprising at least one of the following steps:
   a. providing said switching module additionally comprising at least one switch configured to reversibly connect said energy generator to at least one of said N electrodes; and simultaneously connecting M electrodes to said energy generator via said at least one switch;
   b. selecting the range for the ratio M/N from a group consisting of: for N>10, 1/N to 10%; 10% to 25%; and greater than 25%;
   c. selecting N to be 40;
   d. providing at least one of said N electrodes with between 2 and 5 of said at least two protruding conducting elements; and,
   e. providing at least one of said N electrodes with 4 of said at least two protruding conducting elements.

13. The method of claim 9, wherein said protruding conducting element is shaped substantially as a triangular prism characterized by a rectangle base of length L and width W, two four-sided side faces of length L, two four-sided end faces of said length L and hypotenuse B, and two three-sided end faces of said height A, a hypotenuse B and width W, said base conjoined with said electrode; further wherein said method additionally comprising at least one of the following steps:
   a. selecting said length L to be 150 µm;
   b. selecting the angle θ subtended by the distal end of the end faces of the two four-sided end faces of said length L and hypotenuse B to be in a range of 10° to 50°;
   c. selecting the angle θ subtended by the distal end of the end faces of the two four-sided and faces of said length L and hypotenuse B to be 30°; and,
   d. selecting the shape of said side faces of said triangular prism from a group consisting of flat, inwardly curving, outwardly curving and any combination thereof.

14. The method of claim 9, additionally comprising at least one of the following steps:
a. disposing of said treatment tip;
b. reusing said applicator;
and any combination thereof.

15. The method of claim 9, additionally comprising a step of connecting said N electrodes to said energy generator by means of at least one selected from a group consisting of N second switches, N resistors and any combination thereof.

16. A reusable handheld applicator for fractional skin treatment, comprising:
an energy generator configured to generate energy to be applied to skin tissue;
at least one switching module to control transfer of energy to the N electrodes, so as to provide fractional RF treatment of the skin;
a disposable treatment tip; and
a control unit to control transfer of energy to the skin tissue, by control of the energy generator and the at least one switching module;
wherein said at least one switching module comprises a first line, a return line, N switches and N resistors,
said first line and said return line electrically connectable to said energy generator; and for each pth switch, $1<p<N$,
said pth switch is electrically connected on a first side to said first line;
said pth switch is electrically connected on a second side to a pth resistor and, said treatment tip being connected to said applicator, electrically connected to a pth electrode;
said pth switch is configured, when open, to enable passage of electric current from said energy generator through said first line and through said switch to said pth electrode, and from said pth electrode through said return line to said energy generator; and
said pth switch configured, when closed, to prevent passage of electric current from said energy generator to said pth electrode;
a resistance of each of said N resistors is configured to generate a return path of current from said pth electrode via all other of said N electrodes, said current being divided between said all other of said N electrodes, distributing said current homogeneously across said all other of said N electrodes and minimizing pain to a user.

17. The reusable handheld applicator of claim 16, wherein the disposable treatment tip has different shapes and sizes and wherein the size of the treatment tip defines the treated area of the skin.

18. The reusable handheld applicator of claim 17 wherein the different shapes and sizes of the disposable treatment tips used with the reusable handheld applicator maintain a total impedance constant and effectiveness of the device is unaffected by change of the disposable treatment tip.

19. The reusable handheld applicator of claim 16, wherein each of the electrodes includes 1 to 5 of said at least two protruding conducting elements and wherein a distance between the at least two protruding conducting elements is 1 mm.

20. The reusable handheld applicator of claim 19, wherein each of the N electrodes is shaped like a triangular prism with one facet given by expression $A=W/(2\tan(\theta/2))$ and another facet given by expression $B=W/(2\sin(\theta/2))$, wherein W is the width of the base of the triangular prism.

21. A method of fractional skin RF treatment comprising:
applying to a treated segment of skin an applicator including a matrix of N electrodes located at discrete physically distant from each other locations; and
supplying at least one RF voltage pulse to excite each of said N electrodes at least once during a treatment;
wherein, in each of said at least one RF voltage pulse, at least one of said N electrodes is excited, said at least one of said N electrodes excited in each of said at least one RF voltage pulse is at a discrete position physically distant from an at least one of said N electrodes excited in a previous RF voltage pulse;
wherein a physical distance between said at least one of said N electrodes excited in each of said at least one RF voltage pulse minimizes further RF heating in a discrete volume of tissue already heated by said previous RF voltage pulse, thereby preventing overheating of tissue; wherein said method additionally comprising steps of providing at least one switching configured to enable said at least one of said N skin-penetrating electrically conducting element to be excited, said at least one switching module comprising module with a first line, a return line, N switches and N resistors,
said first line and said return line electrically connectable to said energy generator; and
for each pth switch, $1<p<N$,
said pth switch is electrically connected on a first side to said first line;
said pth switch is electrically connected on a second side to a pth resistor and, said treatment tip being connected to said applicator, electrically connected to a pth electrode;
said pth switch is configured, when open, to enable passage of electric current from said energy generator through said first line and through said switch to said pth electrode, and from said pth electrode through said return line to said energy generator; and
said pth switch configured, when closed, to prevent passage of electric current from said energy generator to said pth electrode;
a resistance of each of said N resistors is configured to generate a return path of current from a pth electrode via all other of said N electrodes, said current being divided between said all other of said N electrodes, distributing said current homogeneously across said all other of said N electrodes and minimizing pain to a user.

22. The method of claim 21, wherein the energy in at least one of said at least one RF voltage pulse comprises more than one frequency, the more than one frequency and energy delivered variable during said at least one pulse.

23. The method of claim 21, wherein each of said N electrodes operates in a single frequency pulse selected from a plurality of frequencies delivered to the each of said N electrodes.

24. The method of claim 21, wherein a duration of said at least one RF voltage pulse is between 5 ms and 30 ms, and an RMS voltage of said at least one RF voltage pulse is between 220 V and 280 V.

25. The method of claim 21, wherein a shape of the N electrodes is a triangular prism with a shape of one facet given by expression $A=W/(2\tan(\theta/2))$ and a shape of another facet given by expression $B=W/(2\sin(\theta/2))$, W being a width of a base of said triangular prism.

26. The method of claim 25, additionally comprising a step of, to minimize pain to a treated subject, selecting said angle $\theta$ of the protruding conducting elements to be 30°.

27. The method of claim 21, additionally comprising configuring the treatment tip to be covering an area of a lesion to create a predefined energy distribution along the lesion.

* * * * *

UNITED STATES PATENT AND TRADEMARK OFFICE
CERTIFICATE OF CORRECTION

PATENT NO. : 11,197,713 B2
APPLICATION NO. : 14/251937
DATED : December 14, 2021
INVENTOR(S) : Boris Vaynberg and Yotam Zimmerman It is certified that error appears in the above-identified patent and that said Letters Patent is hereby corrected as shown below:

In the Claims

Claim 1, Column 19, Line 44: Please delete "open" and replace with "closed".
Claim 1, Column 19, Line 49: Please delete "closed" and replace with "open".

Claim 9, Column 22, Line 52: Please delete "open" and replace with "closed".
Claim 9, Column 22, Line 58: Please delete "closed" and replace with "open".

Claim 16, Column 25, Line 34: Please delete "open" and replace with "closed".
Claim 16, Column 25, Line 39: Please delete "closed" and replace with "open".

Claim 21, Column 26, Line 33: Please delete "open" and replace with "closed".
Claim 21, Column 26, Line 38: Please delete "closed" and replace with "open".

Signed and Sealed this
Twenty-third Day of August, 2022

Katherine Kelly Vidal
*Director of the United States Patent and Trademark Office*